(12) United States Patent
Kim et al.

(10) Patent No.: US 10,292,932 B2
(45) Date of Patent: May 21, 2019

(54) POLYMERIC MICELLE PARTICLE COMPRISING ANIONIC DRUGS AND METHOD OF PREPARING THE SAME

(71) Applicant: SAMYANG BIOPHARMACEUTICALS CORPORATION, Seoul (KR)

(72) Inventors: Se-Ho Kim, Daejeon (KR); Ji-Yeon Son, Gimhae (KR); Muhn-Ho La, Daejeon (KR); Sung-Won Choi, Daejeon (KR); Min-Hyo Seo, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 15/137,167

(22) Filed: Apr. 25, 2016

(65) Prior Publication Data

US 2016/0228361 A1     Aug. 11, 2016

Related U.S. Application Data

(63) Continuation-in-part of application No. 13/141,101, filed as application No. PCT/KR2009/007804 on Dec. 24, 2009, now abandoned.

(30) Foreign Application Priority Data

Dec. 26, 2008    (KR) .......................... 10-2008-0134459
Dec. 24, 2009    (KR) .......................... 10-2009-0130794

(51) Int. Cl.
*A61K 47/34*     (2017.01)
*C12N 15/11*     (2006.01)
(Continued)

(52) U.S. Cl.
CPC .......... *A61K 9/1075* (2013.01); *A61K 9/1271* (2013.01); *A61K 31/7105* (2013.01);
(Continued)

(58) Field of Classification Search
CPC .. A61K 9/1075; A61K 9/1107; A61K 9/1271; A61K 47/34; C12N 15/11; C12N 15/111
See application file for complete search history.

(56) References Cited

U.S. PATENT DOCUMENTS

2010/0297242 A1 * 11/2010 Park ..................... A61K 9/1275
                                                             424/489

FOREIGN PATENT DOCUMENTS

| WO | WO 05/007196 | * | 1/2005 |
| WO | WO 05/107813 | * | 11/2005 |
| WO | WO 09/051451 | * | 4/2009 |

OTHER PUBLICATIONS

Li and Huang, Ann. N. Y. Acad. Sci. 1082:1-8, 2006.*
(Continued)

*Primary Examiner* — Kevin K Hill
(74) *Attorney, Agent, or Firm* — Lex IP Meister, PLLC

(57) ABSTRACT

Disclosed are an anionic drug-containing polymeric micelle particle comprising: an anionic drug as an active ingredient; a cationic lipid; and an amphiphilic block copolymer, wherein the anionic drug forms a complex with the cationic lipid, and the complex is entrapped in the micelle structure of the amphiphilic block copolymer, and a method for preparing the same. The particle may increase stability of the anionic drug in blood or in a body fluid, and it may enable intracellular delivery to improve efficacy of anionic drugs.

16 Claims, 9 Drawing Sheets

Specification includes a Sequence Listing.

(51) Int. Cl.
*A61K 9/107* (2006.01)
*A61K 31/7105* (2006.01)
*A61K 9/127* (2006.01)
*A61K 47/24* (2006.01)
*A61K 9/00* (2006.01)

(52) U.S. Cl.
CPC .............. *A61K 47/24* (2013.01); *A61K 47/34* (2013.01); *C12N 15/111* (2013.01); *A61K 9/0019* (2013.01); *C12N 15/11* (2013.01); *C12N 2320/32* (2013.01)

(56) References Cited

OTHER PUBLICATIONS

Pirotton et al, Pharm. Res. 21(8):1471-1479, 2004.*
Krutzfeldt et al, Nature 438:685-689, 2005.*
Harush-Frenkel et al, Biochem. Biophys. Res. Comm. 353: 26-32, 2007; available online Dec. 6, 2006.*

* cited by examiner

SEQUENCE LISTING

<160> NUMBER OF SEQ ID NOS: 4

<210> SEQ ID NO 1
<211> LENGTH: 19
<212> TYPE: RNA
<213> ORGANISM: Artificial Sequence
<220> FEATURE:
<223> OTHER INFORMATION: GFP siRNA sense strand

<400> SEQUENCE: 1
gcaagcugac ccugaaguu					19

<210> SEQ ID NO 2
<211> LENGTH: 19
<212> TYPE: RNA
<213> ORGANISM: Artificial Sequence
<220> FEATURE:
<223> OTHER INFORMATION: GFP siRNA antisense strand

<400> SEQUENCE: 2
aacuucaggg ucagcuugc					19

<210> SEQ ID NO 3
<211> LENGTH: 19
<212> TYPE: RNA
<213> ORGANISM: Artificial Sequence
<220> FEATURE:
<223> OTHER INFORMATION: VEGF siRNA sence strand

<400> SEQUENCE: 3
ggaguacccu gaugagauc					19

<210> SEQ ID NO 4
<211> LENGTH: 19
<212> TYPE: RNA
<213> ORGANISM: Artificial Sequence
<220> FEATURE:
<223> OTHER INFORMATION: VEGF siRNA antisense strand

<400> SEQUENCE: 4
gaucucauca ggguacucc					19

POLYMERIC MICELLE PARTICLE COMPRISING ANIONIC DRUGS AND METHOD OF PREPARING THE SAME

TECHNICAL FIELD OF THE INVENTION

This disclosure relates to an anionic drug-containing polymeric micelle particle, comprising: an anionic drug as an active ingredient; a lipid comprising a cationic lipid; and an amphiphilic block copolymer, wherein the anionic drug forms a complex with the cationic lipid, and the complex is entrapped in the micelle structure of the amphiphilic block copolymer, and a method of preparing the same.

BACKGROUND OF THE INVENTION

Safe and efficient drug delivery technologies have been studied for a long time in the treatment using anionic drugs, particularly nucleic acid, and various delivery systems and delivery technologies have been developed. Particularly, delivery technologies using a viral delivery system using adenovius or retrovirus, etc., and a non-viral delivery system using cationic lipids, cationic polymers, etc. have been developed.

However, a technology using a viral delivery system is exposed to a risk such as non-specific immune reaction, etc., and it is known to have a lot of problems in commercialization due to the complex production process. Therefore, recent studies are progressed toward a non-viral delivery system using cationic lipids or cationic polymers to improve the disadvantages. Although the non-viral delivery system has inferior efficiency to the viral delivery system, it has less side effects and the production cost is inexpensive compared with viral delivery system.

Many studies have been conducted on non-viral delivery system used for delivery of nucleic acid, and most representative examples thereof include a complex of cationic lipid and nucleic acid (lipoplex) and a complex of a polycationic polymer and nucleic acid (polyplex). Many studies on the cationic lipid or polycationic polymer have been progressed because it stabilizes anionic drugs by forming a complex by electrostatic interactions with the anionic drug and facilitates intracellular delivery (De Paula D, Bentley M V, Mahato R I, Hydrophobization and bioconjugation for enhanced siRNA delivery and targeting, RNA 13 (2007) 431-56; Gary D, Puri N, Won Y Y, Polymer-based siRNA delivery: Perspectives on the fundamental and phenomenological distinctions from polymer-based DNA delivery, J Control release 121 (2007) 64-73).

However, if cationic lipids or polycationic polymers studied so far are used in an amount required to obtain sufficient effects, serious toxicity, although less than viral delivery system, may be caused and thus it may be improper for the therapeutic use. And, although a lipid-nucleic acid complex which forms a complex through a bond between a cationic lipid and nucleic acid is widely used in a cell line experiment, it does not form a structure that can be stable in blood, and thus it cannot be used in the living body (see U.S. Pat. No. 6,458,382).

A nucleic acid-cationic liposome complex or a cationic liposome comprising nucleic acid, which is one of the non-viral delivery system commonly used to deliver nucleic acid into the cells in the living body, consists of an amphiphilic lipid, a neutral lipid and a fusogenic lipid, etc., and nucleic acid is attached to the outside of the liposome by electrostatic bond or captured inside (US2003-0073640, WO2005/007196, US2006-0240093). Specifically, WO2005/007196 and US2006-0240093 disclose a nucleic acid-lipid particle, comprising a siRNA, a cationic lipid, a non-cationic lipid and a conjugated lipid that inhibits aggregation of particles selected from the group consisting of a polyethyleneglycol (PEG)-lipid conjugate, a polyamide (ATTA)-lipid conjugate, and combinations thereof. However, the liposome delivery system may be easily captured by reticuloendothelial system (RES) and exhibit side effects with significant toxicity, and thus, it may not be appropriate for systemic application. And, another non-viral delivery system commonly used includes a cationic polymer, and a polycationic polymer including multivalent cationic charge per a polymer is predominantly used therefore. Particularly, commonly used polymer is polycationic polyethyleneimine (PEI), and the polycationic polymer binds with nucleic acid material by electrostatic interaction to form a nucleic acid-polymer complex thereby forming a nanoparticle. However, the polycationic polymer such as polyethyleneimine promotes apoptosis, and it is known that cytotoxicity increases as the molecular weight and the degree of branching of the polymer increase. Although polycationic polymers with low molecular weight are known to have low cytotoxicity, they cannot form an effective complex due to low charge density of the polymer, and thus, they cannot show the sufficient intracellular delivery and the sufficient stability in blood.

Therefore, it is required to develop an anionic drug delivery technology using the minimal amount of cationic polymer or cationic lipid to decrease toxicity, which is stable in blood and body fluid, and enables intracellular delivery to obtain sufficient effects. The delivery system using the nucleic acid material directly conjugated with a lipid or a polymer is being studied, but if a lipid or a polymer is directly conjugated with nucleic acid material, there are difficulties in terms of conjugation efficiency or quality control.

Meanwhile, there have been various attempts to use amphiphilic block copolymer as a drug delivery system that can solubilize a poorly water-soluble drug by forming a polymeric micelle and stabilize a poorly water-soluble drug in an aqueous solution (Korean Registered Patent No. 08180334). However, since the amphiphilic block copolymer cannot enclose hydrophilic drug such as nucleic acid in the polymeric micelle, it is not suitable for delivery of anionic drug including nucleic acid.

Meanwhile, many diseases result from the overexpression of disease genes or the expression of mutated genes. Since siRNA (short interfering RNA) inhibits the expression of specific genes in a sequence specific manner, it is highlighted as a therapeutic nucleotide drug. Particularly, siRNA is expected to overcome the problems of the antisense nucleotide or ribozyme because siRNA has more potency and more accurate gene selectivity compared with the antisense nucleotide or ribozyme. The siRNA is a short double-stranded RNA molecule and the number of nucleotides in each strand ranges from 15 to 30, and it inhibits the expression of corresponding gene by cleaving mRNA of gene with a sequence complementary thereto (McManus and Sharp, Nature Rev. Genet. 3:737 (2002); Elbashir, et al., Genes Dev. 15:188 (2001).

However, despite these advantages, siRNA is known to be rapidly degraded by nuclease in blood and rapidly excreted from the body through a kidney. It is also known that siRNA cannot easily pass a cell membrane because it is strongly negatively charged. Therefore, to use siRNA as a therapeutic agent, it is required to develop a delivery system that may stabilize siRNA in blood, may efficiently deliver it into target cells, and does not show toxicity.

DETAILED DESCRIPTION OF THE INVENTION

Technical Problem

Accordingly, one aspect of the present invention provides a polymeric micelle particle capable of effectively delivering anionic drugs in the body.

Another aspect of the present invention provides a method of preparing the polymeric micelle particle capable of effectively delivering anionic drugs in the body.

Technical Solution

The polymeric micelle particle according to the present invention comprises
an anionic drug as an active ingredient;
a lipid comprising a cationic lipid; and
an amphiphilic block copolymer,
wherein the anionic drug forms a complex with the cationic lipid by electrostatic interactions, and the complex of the anionic drug and the cationic lipid is entrapped in the core-shell type polymeric micelle structure of the amphiphilic block copolymer which is an A-B type di-block copolymer comprising a hydrophilic A block forming the shell and a hydrophobic B block forming the core,
wherein the hydrophilic A block is one or more selected from the group consisting of polyalkyleneglycol, polyvinyl alcohol, polyvinyl pyrrolidone, polyacrylamide, and a derivative thereof, and the hydrophobic B block is one or more selected from the group consisting of polyester, polyanhydride, polyamino acid, polyorthoester, and polyphosphazine, and
wherein the particle is free from a conjugated lipid selected from the group consisting of a polyethyleneglycol (PEG)-lipid conjugate, a polyamide (ATTA)-lipid conjugate, and combinations thereof Herein, the term, 'a polyethyleneglycol (PEG)-lipid conjugate,' refers to a conjugate in which the polyethyleneglycol is directly conjugated with the lipid.

According to one embodiment of the present invention, the polymeric micelle particle may further comprise a fusogenic lipid. The particle may be used for delivery of the anionic drug contained as the active ingredient.

Another embodiment provides use of a polymeric micelle particle comprising an anionic drug as an active ingredient; a lipid comprising a cationic lipid; and an amphiphilic block copolymer, wherein the anionic drug forms a complex with the cationic lipid, and the complex is entrapped in the micelle structure of the amphiphilic block copolymer, for delivery of an anionic drug.

Yet another embodiment provides a method of delivering an anionic drug comprising the administration of a polymeric micelle particle comprising: an anionic drug as an active ingredient; a lipid comprising a cationic lipid; and an amphiphilic block copolymer, wherein the anionic drug forms a complex with the cationic lipid, and the complex is entrapped in the micelle structure of the amphiphilic block copolymer, to a patient in need thereof. The patient may include mammals, preferably human, primates, rodents, and the like.

And, a method of preparing the particle according to the present invention may comprise:

(a) dissolving the anionic drug and the cationic lipid in a water-miscible organic solvent or a mixed solvent of an aqueous solution and an organic solvent so as to separate the phases;

(b) separating the organic solvent layer of (a);

(c) mixing the organic solvent of (b) with the amphiphilic block copolymer and removing the organic solvent; and (d) adding an aqueous solution to the mixture from which the organic solvent is removed so as to form a micelle According to another embodiment, a method of preparing the particle according to the present invention may comprise:

(a) dissolving the anionic drug, the cationic lipid and the amphiphilic block copolymer in a water-miscible organic solvent or a mixed solvent of an aqueous solution and an organic solvent;

(b) removing the organic solvent layer of (a); and (c) adding an aqueous solution to the mixture of (b) from which the organic solvent is removed so as to form a micelle.

Hereinafter, the present invention will be explained in detail.

According to one embodiment, the anionic drug and the cationic lipid are entrapped in the micelle structure of the amphiphilic block copolymer while forming a complex of the anionic drug and the lipid by electrostatic interactions.

FIG. 1 schematically shows the structure of the polymeric micelle delivery system according to one embodiment of the present invention in which the anionic drug and the cationic lipid are enclosed. As shown in FIG. 1, the anionic drug binds to the cationic lipid by electrostatic interactions, so as to form a complex of the anionic drug and the cationic lipid, and the formed complex of the anionic drug and the cationic lipid is entrapped in the micelle structure of the amphiphilic block copolymer.

When the complex of the anionic drug and the cationic lipid is entrapped in the micelle structure of the amphiphilic block copolymer, it may have improved stability in blood or in a body fluid. According to one embodiment, the particle size of the micelle may be 10 to 200 nm, specifically 10 to 150 nm, more specifically, 10 to less than 100 nm. The particle size is determined considering the stability of the micelle structure, the contents of the constitutional ingredients, absorption of anionic drugs in the body, and convenience of sterilization as a pharmaceutical composition.

The anionic drug may include any material that is negatively charged in an aqueous solution and has pharmacological activity. According to one embodiment, the anionic property may be provided from at least one functional group selected from the group consisting of carboxylic group, phosphate group, and sulfate group. According to one embodiment, the anionic drug may be a multi-anionic drug or nucleic acid.

The nucleic acid may be a nucleic acid drug such as polynucleotide derivatives wherein deoxyribonucleic acid, ribonucleic acid or backbone, sugar or base is chemically modified or the end is modified, and more specific examples may include RNA, DNA, siRNA (short interfering RNA), aptamer, antisense ODN (oligodeoxynucleotide), antisense RNA, ribozyme, DNAzyme, and a combination thereof. And, the backbone, sugar or base of the nucleic acid may be modified or the end may be modified for the purpose of increasing blood stability or weakening immune reactions, and the like. Specifically, a part of phosphodiester bond of nucleic acid may be substituted by phosphorothioate or boranophosphate bond, or at least one kind of nucleotide wherein various functional groups such as methyl group, methoxyethyl group, fluorine, and the like are introduced in 2'-OH positions of a part of ribose bases may be included.

According to another embodiment, the end of the nucleic acid may be modified by at least one selected from the group consisting of cholesterol, tocopherol, and C10-C24 fatty acid. For example, for siRNA, 5'end or 3'end, or both ends of sense and/or antisense strand may be modified, and preferably, the end of sense strand may be modified.

The cholesterol, tocopherol and fatty acid may include analogues, derivatives and metabolites thereof.

The siRNA refers to duplex RNA or single strand RNA having a double stranded form in the single strand RNA, which may reduce or inhibit the expression of a target gene by mediating degradation of mRNA complementary to the sequence of siRNA if siRNA exists in the same cell as the target gene does. The bond between the double strands is made by hydrogen bond between nucleotides, not all nucleotides in the double strands should be complementarily bound with the corresponding nucleotides, and both strands may be separated or may not be separated. According to one embodiment, the length of the siRNA may be about 15-60 nucleotides (it means the number of nucleotides of one of double stranded RNA, i.e., the number of base pairs, and in the case of a single stranded RNA, it means the length of double strands in the single stranded RNA), specifically about 15-30 nucleotides, and more specifically about 19-25 nucleotides.

According to one embodiment, the double stranded siRNA may have overhang of 1-5 nucleotides at 3' or 5' end or both ends. According to another embodiment, it may be blunt without overhang at both ends. Specifically, it may be siRNA disclosed in US20020086356 and U.S. Pat. No. 7,056,704 (incorporated herein by references).

According to one embodiment, siRNA may have a symmetrical structure with the same lengths of two strands, or it may have a non-symmetrical structure with one strand shorter than the other strand. Specifically, it may be a non-symmetrical siRNA (small interfering RNA) molecule of double strands consisting of 19-21 nucleotide (nt) antisense; and 15~19 nt sense having a sequence complementary to the antisense, wherein 5'end of the antisense is blunt end, and the 3'end of the antisense has 1-5 nucleotide overhang. Specifically, it may be siRNA disclosed in WO09/078685 (incorporated herein by reference).

The anionic drug of the present invention may be included in the content of 0.001 to 10 wt %, specifically 0.01 to 5 wt %, based on the total weight of the particle. If the content is less than 0.001 wt %, the amount of delivery system is too large compared to the drug, and thus, side effect may be caused by delivery system, and if it exceeds 10 wt %, the size of micelle may be too large to decrease stability of the micelle and increase loss rate during filter sterilization.

According to one embodiment, the cationic lipid forms a complex with the anionic drug by electrostatic interactions, and the complex is entrapped in the micelle structure of the amphiphilic block copolymer. The cationic lipid may include any lipid capable of forming a complex with the anionic drug by electrostatic interactions, and specific example thereof may include N,N-dioleyl-N,N-dimethylammoniumchloride (DODAC), N,N-distearyl-N,N-dimethyl-ammoniumbromide (DDAB), N-(1-(2,3-dioleoyloxy)propyl-N,N,N-trimethylammoniumchloride (DOTAP), N,N-dimethyl-(2,3-dioleoyloxy)propylamine (DODMA), 1,2-diacyl-3-trimethylammonium-propane (TAP), 1,2-diacyl-3-dimethylammonium-propane (DAP), 3β-[N—(N',N',N'-trimethylaminoethane)carbamoyl]cholesterol (TC-cholesterol), 3β[N—(N',N'-dimethylaminoethane)carbamoyl]cholesterol (DC-cholesterol), 3β[N—(N'-monomethylaminoethane)carbamoyl]cholesterol (MC-cholesterol), 3β[N-(aminoethane)carbamoyl]cholesterol (AC-cholesterol), cholesteryloxypropane-1-amine (COPA), N—(N'-aminoethane)carbamoylpropanoic tocopherol (AC-tocopherol), N—(N'-methylaminoethane)carbamoylpropanoic tocopherol (MC-tocopherol), and a combination thereof. Specifically, to decrease toxicity induced by cationic lipid, it may be preferable to use less polycationic lipid having high charge density, and more specifically, one functional group capable of exhibiting positive charge in the molecule in an aqueous solution may be included.

Specific example of the cationic lipid may include 3β-[N—N—(N',N',N'-trimethylaminoethane)carbamoyl]cholesterol (TC-cholesterol), 3β[N—(N',N'-dimethylaminoethane)carbamoyl]cholesterol (DC-cholesterol), 3β[N—(N'-monomethylaminoethane)carbamoyl]cholesterol (MC-cholesterol), 3β[N-(aminoethane)carbamoyl]cholesterol (AC-cholesterol), N-(1-(2,3-dioleoyloxy)propyl-N,N,N-trimethylammoniumchloride (DOTAP), N,N-dimethyl-(2,3-dioleoyloxy)propylamine (DODMA), N,N,N-trimethyl-(2,3-dioleoyloxy)propylamine (DOTMA), and a combination thereof.

The cationic lipid may be included in the content of 0.01 to 50 wt %, specifically 0.1 to 15 wt %, more specifically 1 to 10 wt %, based on the total weight of the particle. If the content is less than 0.01 wt %, it may not be sufficient to form a complex with the anionic drug, and if it exceeds 50 wt %, the size of micelle may be too large to decrease stability of the micelle and increase loss rate during filter sterilization.

The cationic lipid binds with the anionic drug by electrostatic interactions so as to form a complex with the anionic drug. According to one embodiment, the ratio of quantity of electric charge of the cationic lipid (N) and the anionic drug (P) (N/P: the ratio of the positive electric charge of the cationic lipid to the negative electric charge of the anionic drug) is 0.1 to 128, specifically 0.5 to 36, more specifically 1 to 21. If the ratio (N/P) is less than 0.1, it may be difficult to form a complex including a sufficient amount of anionic drug. On the other hand, if the ratio (N/P) exceeds 128, toxicity may be induced.

According to one embodiment, the amphiphilic block copolymer may be an A-B type block copolymer including a hydrophilic A block and a hydrophobic B block. The A-B type block copolymer forms a core-shell type polymeric micelle in an aqueous solution, wherein the hydrophobic B block forms a core and the hydrophilic A block forms a shell.

According to one embodiment, the hydrophilic A block may be at least one selected from the group consisting of polyalkyleneglycol, polyvinyl alcohol, polyvinyl pyrrolidone, polyacrylamide, and a derivative thereof. More specifically, the hydrophilic A block may be at least one selected from the group consisting of monomethoxy polyethylene glycol, monoacetoxy polyethylene glycol, polyethylene glycol, a copolymer of polyethylene and propylene glycol, and polyvinyl pyrrolidone. According to another embodiment, the hydrophilic A block may have a number average molecular weight of 200 to 50,000 Dalton, specifically 1,000 to 20,000 Dalton, more specifically 1,000 to 5,000 Dalton.

And, if necessary, a functional group or a ligand that may bind to a specific tissue or cell, or a functional group capable of promoting intracellular delivery may be chemically conjugated to the end of the hydrophilic A block so as to control the distribution of the polymeric micelle delivery system in the body or increase the efficiency of the intracellular delivery of polymeric micelle delivery system. The functional group or ligand may include monosaccharide, polysaccharide, vitamins, peptides, proteins, an antibody to a cell surface receptor, and a combination thereof. More specific examples thereof may include anisamide, vitamin B9 (folic acid), vitamin B12, vitamin A, galatose, lactose, mannose, hyaluronic acid, RGD peptide, NGR peptide, transferrin, an antibody to a transferring receptor, and a combination thereof.

The hydrophobic B block is a polymer having excellent biocompatibility and biodegradability, and it may be at least one selected from the group consisting of polyester, polyanhydride, polyamino acid, polyorthoester, and polyphosphazine. More specific examples thereof may include polylactide, polyglycolide, polycaprolactone, polydioxane-2-one, a copolymer of polylactide and glycolide, a copolymer of polylactide and polydioxane-2-one, a copolymer of polylactide and polycaprolactone, a copolymer of polyglycolide and polycaprolactone, and a combination thereof. According to one embodiment, the hydrophobic B block may have a number average molecular weight of 50 to 50,000 Dalton, specifically 200 to 20,000 Dalton, more specifically 1,000 to 5,000 Dalton. And, to increase hydrophobicity of the hydrophobic block for improving the stability of the micelle, tocopherol, cholesterol, or C10-C24 fatty acid may be chemically conjugated to a hydroxyl group of the hydrophobic block end. In a preferable embodiment, the content of tocopherol, cholesterol, or C10-C24 fatty acid ranges from 4.5 to 10.5%, for example, 4.5% or 10.4%, by weight based on the weight of the amphiphilic block copolymer.

The amphiphilic block copolymer comprising the hydrophilic block (A) and the hydrophobic block (B) may be included in the content of 40 to 98 wt %, specifically 50 to 95 wt %, more specifically 65 to 90 wt %, based on the total dry weight of the particle. If the content of the amphiphilic block copolymer is less than 40 wt %, the size of the micelle may become so large that the stability of the micelle may be decreased and the loss during filter sterilization may be increased, and if it exceeds 98 wt %, the content of anionic drug that can be incorporated may become too small.

The particle according to an embodiment of the invention is based on a polymer, particularly, an amphiphilic block copolymer comprising a hydrophilic A block and a hydrophobic B block, so may feature a major portion of the amphiphilic block copolymer. The weight ratio of the amphiphilic block copolymer to the lipid may be greater than 1, for example, ranging from 1.5 to 20, particularly, 2 to 15, and more particularly, 3 to 10.

According to another embodiment, the amphiphilic block copolymer may include 40 to 70 wt % of the hydrophilic block (A), specifically 50 to 60 wt % of the hydrophilic block (A), based on the weight of the copolymer. If the ratio of the hydrophilic block (A) is less than 40 wt %, solubility of the polymer in water is low, and thus it may be difficult to form a micelle. On the other hand, if it exceeds 70 wt %, hydrophilicity may be too high and thus stability of the polymeric micelle is low, and it may be difficult to solubilize a complex of the anionic drug and the cationic lipid.

According to one embodiment, the amphiphilic block copolymer allows enclosure of the complex of the anionic drug and the cationic lipid in the micelle structure in an aqueous solution, wherein the ratio of the weight of the complex of the anionic drug and the cationic lipid (a) to the weight of the amphiphilic block copolymer (b) [a/b×100; (the weight of the anionic drug+the weight of the cationic lipid)/the weight of the amphiphilic block copolymer×100] may be 0.001 to 100 wt %, specifically 0.01 to 50 wt %, more specifically 0.1 to 10%. If the weight ratio is less than 0.001 wt %, the content of the complex of the anionic drug and the cationic lipid may become too low, and thus it may be difficult to satisfy effective content of the anionic drug, and if it exceeds 100 wt %, a micelle structure of appropriate size may not be formed considering the molecular weight of the amphiphilic block copolymer and the amount of the complex of the anionic drug and the lipid.

According to one embodiment, the polymeric micelle particle of the present invention may further comprise a fusogenic lipid in the content of 0.01 to 50 wt %, specifically 0.1 to 10 wt %, based on the total weight of the particle, in order to increase intracellular delivery efficiency of the anionic drug. In a preferable embodiment, the weight ratio of the fusogenic lipid to the cationic lipid ranges from 0.1 to 10 particularly 0.2 to 5, and more particularly, 0.5 to 3.

The fusogenic lipid form a complex with the anionic drug, the cationic lipid by the hydrophobic interactions while mixing the anionic drug with the cationic lipid, and the complex comprising the fusogenic lipid is entrapped in the micelle structure of the amphiphilic block copolymer. According to one embodiment, the fusogenic lipid may be phospholipid, cholesterol, tocopherol, or a combination thereof.

Specifically, the phospholipid may be selected from phosphatidylethanolamin (PE), phosphatidylcholine (PC), phosphatidic acid, or a combination thereof. The phosphatidylethanolamin (PE), phosphatidylcholine (PC) and the phosphatidic acid may be bound to one or two C10-24 fatty acid. The cholesterol and tocopherol may include analogues, derivative, and metabolites thereof.

Specifically, the fusogenic lipid may include dilauroyl phosphatidylethanolamine, dimyristoyl phosphatidylethanolamine, dipalmitoyl phosphatidylethanolamine, distearoyl phosphatidylethanolamine, dioleoyl phosphatidylethanolamine, dilinoleoyl phosphatidylethanolamine, 1-palmitoyl-2-oleoyl phosphatidylethanolamine, 1,2-diphytanoyl-3-sn-phosphatidylethanolamine, dilauroyl phosphatidylcholine, dimyristoyl phosphatidylcholine, dipalmitoyl phosphatidylcholine, distearoyl phosphatidylcholine, dioleoyl phosphatidylcholine, dilinoleoyl phosphatidylcholine, 1-palmitoyl-2-oleoyl phosphatidylcholine, 1,2-diphytanoyl-3-sn-phosphatidylcholine, dilauroyl phosphatidic acid, dimyristoyl phosphatidic acid, dipalmitoyl phosphatidic acid, distearoyl phosphatidic acid, dioleoyl phosphatidic acid, dilinoleoyl phosphatidic acid, 1-palmitoyl-2-oleoyl phosphatidic acid, 1,2-diphytanoyl-3-sn-phosphatidic acid, cholesterol, tocopherol, and a combination thereof.

According to preferred embodiment, the fusogenic lipid may include dioleoyl phosphatidylethanolamine (DOPE), 1,2-dipalmitoleoyl-sn-glycero-3-phosphocholine (DPPC), 1,2-dioleoyl-sn-glycero-3-phosphocholine (DOPC), 1,2-dipalmitoleoyl-sn-glycero-3-phosphoethanolamine (DPPE), and a combination thereof.

The present invention also provides a method of preparing a polymeric micelle particle comprising an amphiphilic diblock copolymer micelle containing anionic drug.

According to one embodiment, the method of preparing a polymeric micelle particle comprising an anionic drug, a cationic lipid, and an amphiphilic block copolymer comprises:

(a) dissolving the anionic drug and the cationic lipid in a water-miscible organic solvent or a mixed solvent of an aqueous solution and an organic solvent so as to separate the phases;

(b) separating the organic solvent layer of (a);

(c) mixing the organic solvent of (b) with the amphiphilic block copolymer and removing the organic solvent; and (d) adding an aqueous solution to the mixture from which the organic solvent is removed so as to form a micelle.

In the step (a), the anionic drug and the cationic lipid are mixed in a water-miscible organic solvent, or a mixed solvent of an aqueous solution and an organic solvent to form a complex. Specifically, the water-miscible organic solvent may include acetone, ethanol, methanol, acetic acid, and a combination thereof, and the organic solvent of the mixed solvent may include ethyl acetate, acetonitrile, methylene chloride, chloroform, dioxane, and a combination thereof. The aqueous solution may include distillated water, water for injection, and a buffer solution. The amount of the complex of the anionic drug and the cationic lipid dissolved in the solvent may be 0.1~100 wt %, specifically 0.1~10 wt %, more specifically 0.1~1 wt %, based on the amount of the used solvent. If the amount is 100 wt % or more, yield may be rapidly decreased when the complex of the anionic drug and the cationic lipid is extracted with an organic solvent in the step (b) below.

In the step (b), the complex of the anionic drug and the cationic lipid is recovered by phase separation. An aqueous solution and an organic solvent may be added to the solvent of the step (a) to induce phase separation. And, to shorten the phase separation time, a centrifugation process may be added.

In the step (c), an amphiphilic block copolymer is added to the extracted organic solvent and mixed, and then, the organic solvent is removed by evaporation.

In the step (d), the complex of the anionic drug and the cationic lipid is entrapped in the micelle structure of the amphiphilic block copolymer by dissolving the remaining mixture with an aqueous solution. The aqueous solution may be distillated water, water for injection, or a buffer solution, and the amount may be such that the concentration of the amphiphilic block copolymer may become 10 to 300 mg/mL. If the concentration of the amphiphilic block copolymer is less than 10 mg/mL, the volume of the aqueous solution may become too large thus rendering it difficult to handle during the preparation process, and if it exceeds 300 mg/mL, the viscosity of the aqueous solution may be too high thus rendering it difficult to prepare a micelle.

According to yet another embodiment, a method of preparing a polymeric micelle particle for delivery of an anionic drug comprising an anionic drug, a cationic lipid, and an amphiphilic block copolymer comprises:

(a') dissolving the anionic drug, the cationic lipid and the amphiphilic block copolymer in a water-miscible organic solvent or a mixed solvent of an aqueous solution and an organic solvent;

(b') removing the organic solvent of (a'); and (c') adding an aqueous solution to the mixture of (b') so as to form a micelle.

In the step (a'), the anionic drug, the cationic lipid, and the amphiphilic block copolymer are mixed in a water-miscible organic solvent, or a mixed solvent of an aqueous solution and an organic solvent to form a complex. Specifically, the water-miscible organic solvent may include acetone, ethanol, methanol, acetic acid, and a combination thereof, and the organic solvent of the mixed solvent may include ethyl acetate, acetonitrile, methylene chloride, chloroform, dioxane, and a combination thereof. The aqueous solution may include distillated water, water for injection, and a buffer solution.

In the step (b'), the organic solvent is removed by evaporation.

In the step (c'), the remaining mixture is dissolved in an aqueous solution, thereby enclosing the complex of the complex of the anionic drug and the cationic lipid in the micelle structure of the amphiphilic block copolymer. The kind and the amount of the aqueous solution are as described above.

According to yet another embodiment, for a polymeric micelle particle comprising a fusogenic lipid, the fusogenic lipid may be added together when adding the amphiphilic block copolymer for forming a micelle, and for example, it may be added in the step (c) or (a').

According to yet another embodiment, the method may further comprise (e) adding assistant material for freeze drying, after the step (d) of (c').

According to one embodiment, the method may further comprise sterilizing the polymeric micelle aqueous solution obtained in the step (d) or (c') with a sterilization filter, before the (e) freeze drying.

According to one embodiment, the assistant material for freeze drying may include lactose, mannitol, sorbitol, sucrose, and a combination thereof. The assistant material for freeze drying is added to allow the freeze dried composition to maintain a cake form. According to another embodiment, the content of the assistant material for freeze drying may be 1 to 90 wt %, specifically 10 to 60 wt %, based on the total dry weight of the particle.

According to one embodiment, the amphiphilic block copolymer micelle particle containing an anionic drug may be prepared in the form of an aqueous solution, powder or a tablet. According to another embodiment, the particle may be prepared for injection. For example, the freeze dried particle may be reconstituted with distillated water for injection, a 0.9% saline solution, a 5% dextrose aqueous solution, and the like.

The micelle formed according to the preparation method of the present invention is stable in blood, and has the particle size of 10 to 200 nm, specifically 10 to 150 nm, more specifically 10 to less than 100 nm The polymeric micelle particle containing an anionic drug of the present invention may be administered in the route of blood vessel, muscle, subcutaneous, oral, bone, transdermal or local tissue, and the like, and it may be formulated in various forms such as a solution, a suspension for injection, a tablet, or a capsule, and the like.

The polymeric micelle particle containing an anionic drug of the present invention may increase stability of the anionic drug in blood or in body fluid by isolating the anionic drug from outside using the cationic lipid and the amphiphilic block polymer. And, the particle of the present invention may effectively deliver the anionic drug in the cell. And, the amphiphilic polymer has excellent biodegradability and biocompatibility.

EXAMPLES

Hereinafter, the present invention will be explained in detail with reference to the following Examples, however theses Examples are only to illustrate the invention and the scope of the invention is not limited thereto in any manner

[Example 1] Synthesis of AC-cholesterol(3β[N-(aminoethane)carbamoyl]cholesterol)

To synthesize AC-cholesterol, cholesteryl chloroformate (Sigma-Aldrich) and ethylenediamine (Sigma-Aldrich) were reacted as follows.

1 g (2.23 mmol) of cholesteryl chloroformate was dissolved in 20 ml of chloroform, 20 equivalents of ethylenediamine was diluted with 30 ml of chloroform in a separate reaction vessel, and the temperature was maintained at 4° C. The cholesteryl chloroformate solution was slowly introduced in the reaction vessel containing ethylenediamine, and then, the mixture was reacted at room temperature for 3 hours. After the reaction was completed, the solvent was removed using a rotary evaporator (Buchi, R-2055), and the residue was dissolved again in a small amount of chloroform, and then, extracted with a NaCl saturated solution and $NaCO_3$ to recover a chloroform layer.

And then, the solvent was removed with a rotary evaporator, and the residue was dissolved in chloroform, and then, silica-gel chromatography was conducted to separate. To a fraction eluted with chloroform:methanol=9:1(v/v), a hydrochloric acid solution was added in 50 equivalents of cholesteryl chloroformate, and methanol was gradually added until a single phase was formed so as to form AC-cholesterol hydrochloride.

Figure 1:
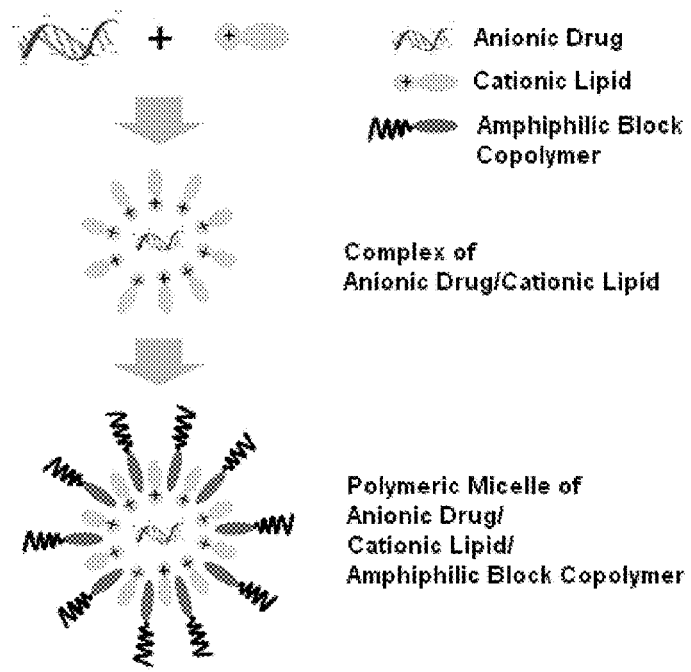
FIG. 1. is a schematic diagram of the polymeric micelle particle containing an anionic drug according to one embodiment of the present invention.
Figure 2:
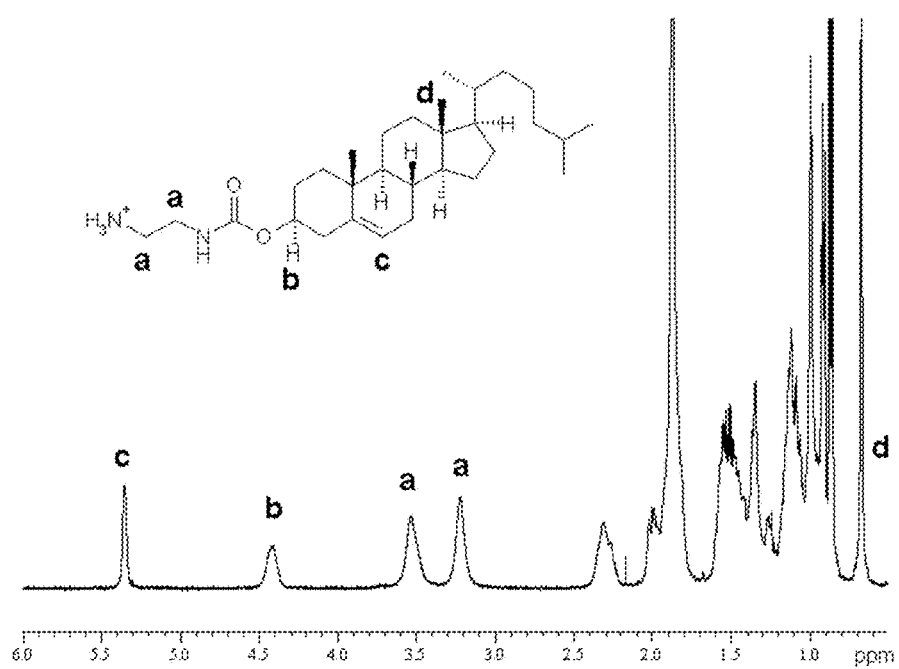
FIG. 2 is an NMR measurement result of AC-tocopherol prepared by the preparation method according to one embodiment of the present invention.

The solvent was completely removed by heating and distillation under reduced pressure with a rotary evaporator. The AC-cholesterol hydrochloride was dissolved in methanol of 60° C., and then, cooled to 4° C. to obtain recrystal. The yield was about 53%. Synthesis and purity of AC-cholesterol were confirmed by $^1$H-NMR, and the result is shown in FIG. 2. The purity was 99% or more.

[Example 2] Synthesis of MC-cholesterol(3β[N—(N'-monomethylaminoethane)carbamoyl]cholesterol)

Figure 3:
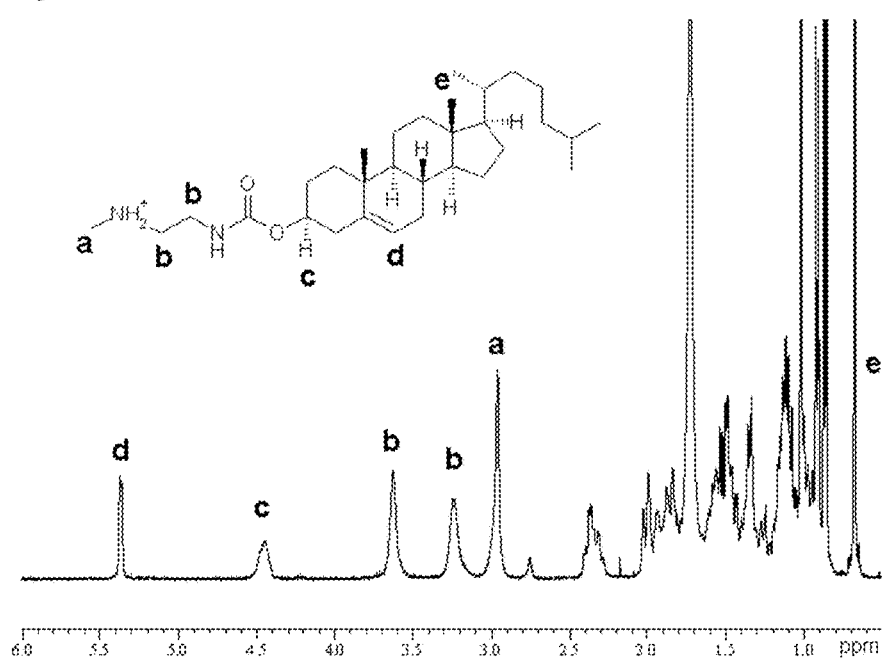
FIG. 3 is an NMR measurement result of MC-tocopherol prepared by the preparation method according to one embodiment of the present invention.

MC-cholesterol was synthesized and purified by the same method as Example 1, except that N-metheylethylenediamine (Sigma-Aldrich) was used in 10 equivalents of cholesteryl chloroformate instead of ethylenediamine. The yield was 62%. Synthesis and purity of AC-cholesterol were confirmed by $^1$H-NMR, and the result is shown in FIG. 3. The purity was 99% or more.

[Example 3] Polymerization of mPEG-PLA (monomethoxy ethylene glycol-polylactide) block copolymer (A-B) (molecular weight 2,000-1,750 Dalton)

5 g of monomethoxy polyethylene glycol (molecular weight 2,000 Dalton or less, NOF corporation) was added to a 100 ml two-necked round bottom flask, and heated to 100° C. under reduced pressure (1 mmHg) for 3 hours to dehydrate. Dry nitrogen was filled in the reaction flask, and a reaction catalyst of stannous octoate ($Sn(Oct)_2$, Sigma-Aldrich) was injected in the amount of 0.1 wt % of lactide (5 mg). The reaction mixture was agitated for 30 minutes, and pressure was reduced to 1 mmHg at 110° C. for 1 hour to remove toluene which is a solvent dissolving the catalyst. Purified lactide (5 g, Purac) was added, and the mixture was heated to 130° C. for 12 hours. The formed polymer was dissolved in ethanol, and diethylether was added to precipitate a polymer. The precipitated polymer was dried in a vacuum oven for 48 hours.

Figure 4:
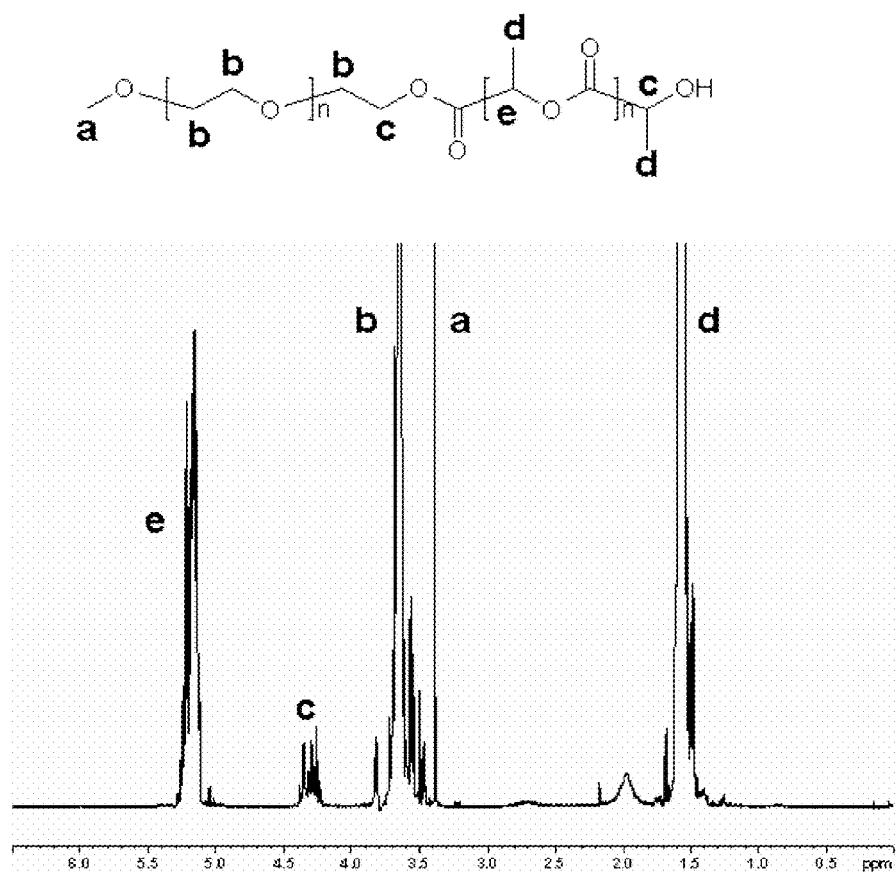
FIG. 4 is an NMR measurement result of mPEG-PLA block copolymer polymerized by the preparation method according to Example 3 of the present invention.

The obtained mPEG-PLA has number average molecular weight of 2,000-1,750 Dalton, and it was confirmed to be of A-B type by $^1$H-NMR in FIG. 4.

[Example 4] Polymerization of mPEG-PLA (monomethoxy polyethylene glycol-polylactide) block copolymer (A-B) (molecular weight 5,000-4,000 Dalton)

Figure 5:
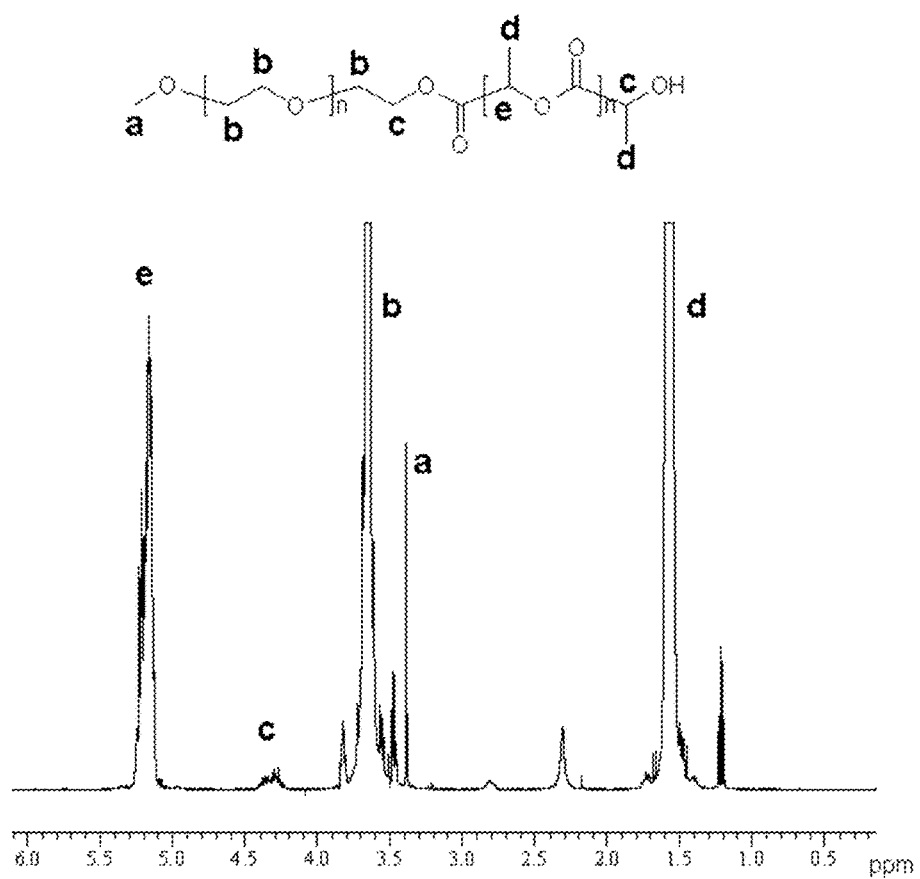
FIG. 5 is an NMR measurement result of mPEG-PLA block copolymer polymerized by the preparation method according to Example 4 of the present invention.

A mPEG-PLA block copolymer having number average molecular weight of 5,000-4,000 Dalton was synthesized by the same method as Example 3, using monomethoxy polyethylene glycol (molecular weight 5,000 Dalton or less, NOF corporation). The $^1$H-NMR measurement results of the obtained mPEG-PLA block copolymer is shown in FIG. 5. As shown in FIG. 5, it is confirmed that the prepared mPEG-PLA block copolymer is of A-B type.

[Example 5] Polymerization of mPEG-PLA-tocopherol (molecular weight 2,000-1,750-530 Dalton)

200 ml of acetonitrile (CAN) was used as a reaction solvent, and 26.4 mmol of mPEG-PLA of Example 3 with number average molecular weight of 2,000-1,750 Dalton and 31.68 mmol of tocopherol succinate (Sigma-Aldrich) as reactants, and 31.68 mmol of dicyclohexyl carbodiimide (DCC, Sigma-Aldrich) and 3.168 mmol of dimethylaminopyridine (DAMP, Sigma-Aldrich) as catalysts were introduced to synthesize at room temperature for 24 hours. The acetonitrile solution in which the reaction product was dissolved was filtered with a glass filter to remove dicyclohexylcarbourea (DCU) produced during the reaction.

Figure 6:
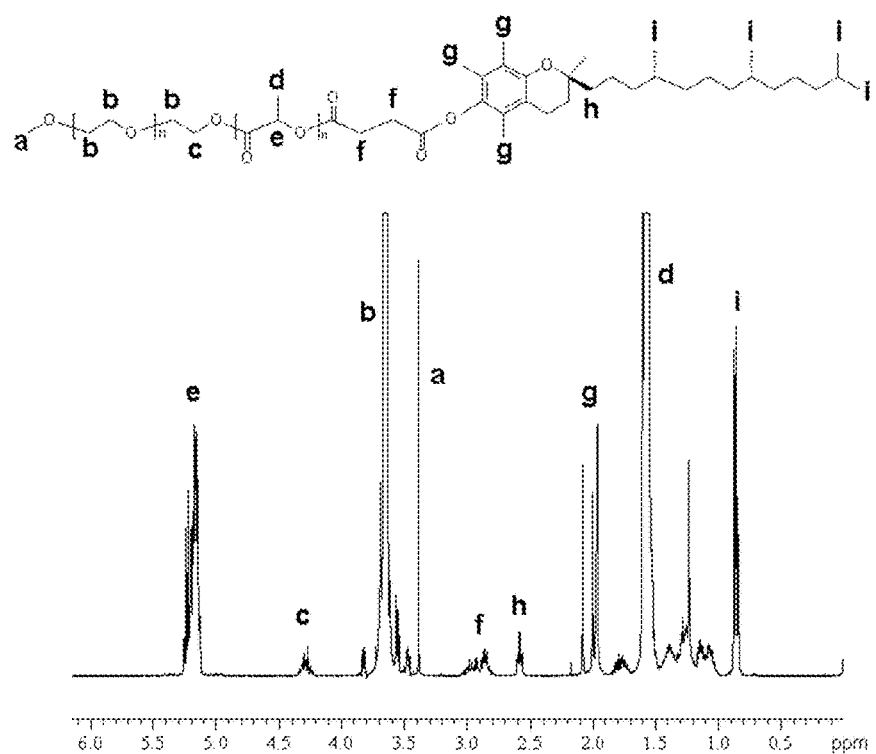
FIG. 6 is an NMR measurement result of mPEG-PLA-tocopherol polymerized by the preparation method according to Example 5 of the present invention.

As a primary purification, the filtered acetonitrile solution was precipitated in a cool mixed solvent of diethylether:hexane=3:7(v/v) to recrystallize a polymer. The obtained polymer was dissolved again in an acetonitrile solution and precipitated in a mixed solvent of diethylether:hexane=3:7 (v/v) to conduct a secondary purification. The purified polymer was vacuum dried to obtain white powder particles. In the $^1$H-NMR analysis of FIG. 6, purity was 97% or more, and yield was 92.7%.

[Example 6] Polymerization of mPEG-PLA-tocopherol (molecular weight 5,000-4,000-530 Dalton)

Figure 7:
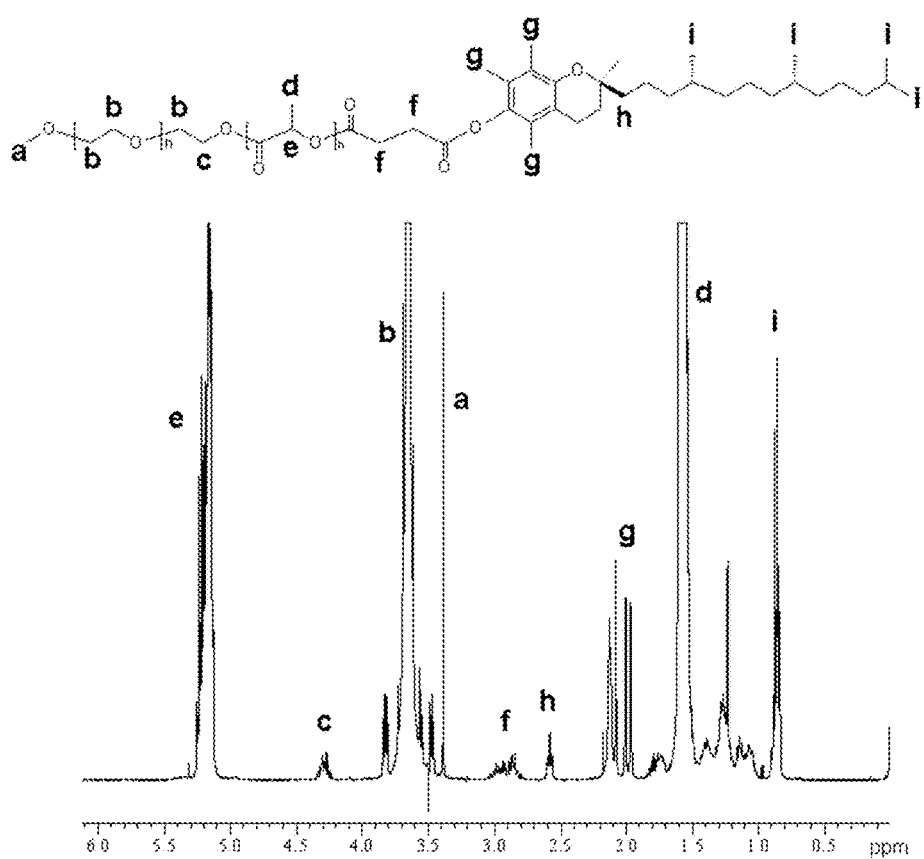
FIG. 7 is an NMR measurement result of mPEG-PLA-tocopherol polymerized by the preparation method according to Example 6 of the present invention.

A mPEG-PLA-tocopherol was polymerized by the same method as Example 5, using mPEG-PLA of Example 4 with number average molecular weight of 5,000-4,000 Dalton. In the $^1$H-NMR analysis of FIG. 7, purity was 97% or more, and the yield was 94.2%.

Figure 8:
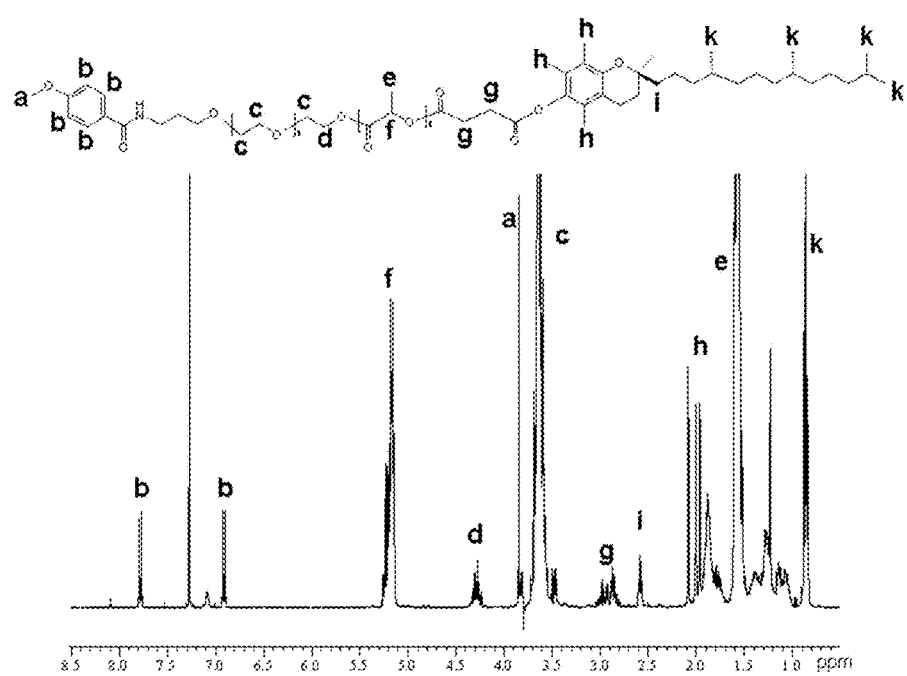
FIG. 8 is an NMR measurement result of anisamide-PEG-PLA polymerized by the preparation method according to one embodiment of the present invention.

[Example 7] Polymerization of Anisamide-PEG-PLA 0.1 g (660 μmol) of anisic acid (4-methoxybenzoic acid, Sigma-Aldrich), 0.146 g (710 μmol) of dicyclohexylcarbodimide (Sigma-Aldrich), and 0.081 g (710 μmol) of N-hydrosuccinimide (NHS, Sigma-Aldrich) were dissolved in a mixed solvent of acetonitrile:dimethylformamide (DMF)=2:1(v/v) and reacted for 24 hours to synthesize anisic acid-NHS ester (AA-NHS), and then, reaction by product of dicyclohexylcarbourea was filtered to remove. 0.519 g (260 μmol) of $H_2N$-PEG-OH (Mn=2,000, NOF corporation) was dissolved in 2 ml of acetonitrile and 1.5 equivalents of AA-NHS was added, and then, the reaction mixture was reacted at room temperature for 24 hours to synthesize anisamide-PEG (AA-PEG). The process of precipitating the reactant in cool diethylether to recrystallize AA-PEG was repeated twice to purify AA-PEG. The process of polymerizing AA-PEG-PLA-tocopherol from AA-PEG was performed by the same method as Examples 5 and 6. In the $^1$H-NMR analysis, introduction rate of anisamide was 90.2%, and the result is shown in FIG. 8.

[Example 8] Preparation of siRNA/cationic Lipid Complex

A siRNA/cationic lipid complex was prepared using Bligh & Dyer extraction method (Bligh, E G., Dyer, W J, A rapid method of total lipid extraction and purification, Can. J. Biochem. Physiol 37 (1959) 911-937). 5 μg of the siRNA was used, and as the cationic lipid, AC-cholesterol, MC-cholesterol and TC-cholesterol (Sigma Aldrich) of Examples 1 and 2 were respectively used 0, 1, 2, 4, 8, and 16 times of the moles of siRNA phosphate groups (N/P ratio (the ratio of cation of the cationic lipid to the phosphate groups of siRNA)=0, 1, 2, 4, 8 and 16).

GFP siRNA sequence (Dharmacon):

```
                        (Sequence ID No. 1)
Sense strand:     5'-GCAAGCUGACCCUGAAGUUdTdT-3'

(Sequence ID No. 2)
Antisense strand: 5'-AACUUCAGGGUCAGCUUGCdTdT-3'
```

100 μl of the siRNA aqueous solution, 100 μl of the cationic lipid chloroform solution and 120 μl of methanol were mixed in the above N/P ratio to form a monophase (Bligh & Dyer monophase), 100 μl of distilled water and 100 μl of chloroform were added to separate the phases. The amount of siRNA in the aqueous solution layer and the chloroform layer were quantified with a Ribogreen reagent (Invitrogen).

TABLE 1

Ratio of the amount of siRNA existing in each phase to the amount of siRNA introduced after phase shift (%)

| N/P ratio | AC-cholesterol Aqueous phase | AC-cholesterol organic phase | MC-cholesterol Aqueous phase | MC-cholesterol Organic phase | TC-cholesterol aqueous phase | TC-cholesterol Organic phase |
|---|---|---|---|---|---|---|
| 0 | 100.8 | 0 | 95.4 | 0 | 99.1 | 0 |
| 1 | 37.7 | 70.9 | 93.3 | 0 | 0 | 97.7 |
| 2 | 0 | 100.1 | 27.5 | 72.7 | 0 | 98.9 |
| 4 | 0 | 106.1 | 0 | 102.2 | 0 | 97.9 |
| 8 | 0 | 105.6 | 0 | 102.8 | 0 | 96.8 |
| 16 | 0 | 114.7 | 0 | 105.4 | 0 | 98.2 |

Referring to Table 1, it is confirmed that the cationic lipids form a complex with siRNA and the siRNA/cationic lipid complex is phase-shifted to the organic solvent layer.

[Example 9] Preparation of siRNA/AC-cholesterol/mPEG-PLA Polymeric Micelle

A siRNA/cationic lipid complex was prepared according to the method of Example 8. The ratio of the cation of AC-cholesterol to the phosphate group of siRNA (N/P ratio) was 6. After phase separation, a chloroform layer was separately collected and added to mPEG-PLA of Example 3 such that the ratio of siRNA/AC-cholesterol complex to mPEG-PLA (molecular weight 2,000-1,750 Dalton) may be 0.51 wt %, and then, the mixture was moved into an 1-necked round flask, and distilled under reduced pressure in a rotary evaporator to remove the solvent. 300 μL of distilled water was added to the flask, and gently shaken to dissolve, thereby preparing a siRNA/AC-cholesterol/mPEG-PLA polymeric micelle delivery system.

[Example 10] Preparation of siRNA/AC-cholesterol/mPEG-PLA-tocopherol Polymeric Micelle A siRNA/AC-cholesterol/mPEG-PLA-tocopherol polymeric micelle delivery system was prepared by the same method of Example 9, except using mPEG-PLA-tocopherol (molecular weight 2,000-1,750-530 Dalton) of Example 5 instead of mPEG-PLA. The ratio of the siRNA/AC-cholesterol complex to mPEG-PLA-tocopherol was 0.51 wt %.

[Example 11] Preparation of siRNA/AC-cholesterol/mPEG-PLA-tocopherol Polymeric Micelle To an one-necked round flask, 46 μg of AC-cholesterol (N/P ratio=6) and ethanol were introduced and completely dissolved at room temperature, and then, 5 μg of siRNA of Example 8 was added and mixed. 9 mg of mPEG-PLA-tocopherol (molecular weight 5,000-4,000-530 Dalton) of Example 6 was added thereto, and agitated at 60° C. for 5 minutes. The ratio of the siRNA/AC-cholesterol complex to mPEG-PLA-tocopherol was controlled to 0.57 wt %.

The mixture was distilled under reduced pressure in a rotary evaporator to remove the solvent. 300 μL of distilled water was added to the flask, and gently shaken to dissolve, thereby preparing a siRNA/AC-cholesterol/mPEG-PLA polymeric micelle delivery system.

[Example 12] Preparation of VEGF siRNA or siRNA-cholesterol/AC-cholesterol/mPEG-PLA-tocopherol Polymeric Micelle VEGF siRNA of the following Sequence ID Nos. 3 and 4 and VEGF siRNA-cholesterol which has a sequence identical to the above sequence but includes cholesterol covalently bonded at 3'end were purchased from Samchully Pharm., and VEFG siRNA and VEGF siRNA-cholesterol polymeric micelle delivery system was prepared by the same method as Example 11.

VEGF siRNA (Dharmacon):

```
                                        (Sequence ID No. 3)
Sense strand:       5'-GGAGUACCCUGAUGAGAUCdTdT-3', (Sequence ID No. 4)
Antisense strand:   5'-GAUCUCAUCAGGGUACUCCdTdT-3'
```

[Example 13] Preparation of siRNA/AC-cholesterol/mPEG-PLA-tocopherol/dioleylphosphatidyl-ethanolamine (DOPE) Polymeric Micelle In the particle of Example 11, 34 μg of DOPE (Avanti polar lipids) was additionally added together with the polymer to prepare a DOPE-containing siRNA polymeric micelle delivery system by the same method as Example 11.

[Experimental Example 1] Measurement of the size of siRNA/cationic lipid/amphiphilic Block Copolymeric Micelle and Confirmation of siRNA Enclosure To confirm whether the siRNA/cationic lipid containing amphiphilic block copolymer forms a nanoparticle, the sizes of siRNA/AC-cholesterol/mPEG-PLA polymeric micelle and siRNA/AC-cholesterol/mPEG-PLA-tocopherol polymeric micelle were measured by DLS (Dynamic Light Scattering) method and described in Table 2.

A helium-neon laser with an output of 10 mV and wavelength of 638 nm was used as a light source, incident light of 90° C. was used, and the experiment was conducted at 25° C. The measurement and analysis were conducted using an ELS-8000 equipment of Photal Otsuka Electronics Co. Ltd.

TABLE 2

|  | Kind of polymer | Weight average particle size |
| --- | --- | --- |
| Example 9 | siRNA/AC-cholesterol/mPEG-PLA | 27.6 ± 16.9 nm |
| Example 10 | siRNA/AC-cholesterol/mPEG-PLA-tocopherol | 26.8 ± 7.2 nm |
| Example 11 | siRNA/AC-cholesterol/mPEG-PLA-tocopherol | 54.5 ± 17.0 nm |
| Example 12 | VEGF siRNA-cholesterol/AC-cholesterol/mPEG-PLA-tocopherol | 60.0 ± 15.4 nm |
| Example 13 | siRNA/AC-cholesterol/mPEG-PLA-tocopherol/DOPE | 82.4 ± 28.5 nm |

The siRNA was quantified in the prepared siRNA/cationic lipid containing amphiphilic block copolymeric micelle by a modified Bligh & Dyer extraction method.

The polymeric micelle delivery systems prepared in each Example was dissolved in 50 mM sodium phosphate, 75 mM NaCl (pH 7.5), and a Bligh & Dyer monophase was formed, and then, extracted with 100 mM sodium phosphate, 150 mM NaCl (pH 7.5) to quantify the siRNA of the aqueous solution layer with a Ribogreen reagent (Invitrogen).

As result of measurement, 90% or more of the siRNA amount could be extracted.

[Experimental Example 2] Blood stability measurement of siRNA/AC-cholesterl/mPEG-PLA-tocopherol Polymeric Micelle To examine how safely the siRNA/AC-cholesterol/mPEG-PLA-tocopherol polymeric micelle protects siRNA in blood, half life of siRNA was measured in blood serum. The polymeric micelle of Example 10 (polymeric micelle 1) and the polymeric micelle of Example 11 (polymeric micelle 2) were cultured at 37° C., in 50% blood serum for the time described in Table 3, and then, the amount of siRNA was quantified to calculate the half life as follows.

To measure the total amount of siRNA of the polymeric micelle, modified Bligh & Dyer method as Experimental Example 1 was performed. The measurement results are described in the following Table 3.

TABLE 3

| Time (min) | Non-enclosed siRNA (%) | siRNA (%) of polymeric micelle 1 | siRNA (%) of polymeric micelle 2 |
| --- | --- | --- | --- |
| 30 | 32.4 | 63.6 | 92.5 |
| 60 | 29.1 | 57.6 | 74.7 |
| 120 | 19.8 | 46.9 | 58.1 |
| 240 | 8.8 | 31.2 | 47.4 |

Referring to Table 3, it is confirmed that the half life of non-enclosed siRNA is 28.4 minutes, while the half life of the siRNA enclosed in the polymeric micelle 1 of Example 10 is 126 minutes and the half life of the siRNA enclosed in the polymeric micelle 2 of Example 11 is 192.5 minutes, and that the half lives of siRNAs increased respectively 4.4 times and 6.8 times compared to the non-enclosed siRNA. It can be seen from the Table 3 that siRNA may be stabilized in blood by enclosing siRNA in a polymeric micelle.

[Experimental Example 3] Stability Evaluation of siRNA or siRNA-cholesterol/AC-cholesterol/mPEG-PLA-tocopherol Polymeric Micelle to RNase It was examined how safely a siRNA or siRNA-cholesterol/AC-cholesterol/mPEG-PLA-tocopherol containing particle protects siRNA to RNase. The polymeric micelle of Example 11 (polymeric micelle 2) and the siRNA-cholesterol polymeric micelle of Example 12 (polymeric micelle 3) were cultured with 10U RNase VI (Promega) for the time described in Table 4, and then, the amount of siRNA was quantified by the same method as Experimental Example 1. The measurement result is described in the following Table 4.

TABLE 4

| Time (min) | Amount of non-enclosed siRNA (%) | siRNA amount of polymeric micelle 2 (siRNA) (%) | Amount of non-enclosed siRNA-cholesterol (%) | siRNA amount of polymeric micelle 3 (siRNA-cholesterol) (%) |
|---|---|---|---|---|
| 40 | 0 | 58.6 | 3.9 | 103.0 |
| 70 | 0 | 53.2 | 3.7 | 101.7 |
| 130 | 0 | 40.3 | 2.4 | 103.4 |

Referring to Table 4, it can be seen that the non-enclosed siRNA was completely degrade within 40 minutes after RNase treatment, while if the siRNA is enclosed in the polymeric micelle, about 40% remained stably even 130 minutes after RNase treatment. Meanwhile, it can be seen that siRNA-cholesterol has slightly higher stability than siRNA in non-enclosed states, and that if the siRNA-cholesterol is enclosed in the polymeric micelle (polymeric micelle 3), stability much increased compared to the siRNA enclosed in the polymeric micelle (polymeric micelle 2). Thus, it can be seen from the Table 4 that siRNA could be stabilized to RNase by enclosing siRNA in the polymeric micelle, and that the effect is more exhibited for siRNA-cholesterol.

[Experimental Example 4] Evaluation of Activity of siRNA/AC-cholesterol/mPEG-PLA-tocopherol polymeric Micelle (Protein Level)

An A549 GFP cell line expressing GFP (Green fluorescence protein) [commonly prepared from A549 cell line (ATCC)] was treated with the GFP siRNA/AC-cholesterol/mPEG-PLA-tocopherol polymeric micelles. And then, intracellular delivery capacity of the polymeric micelle was measured by measuring fluorescence shown by the expression of GFP protein.

The compositional ratio of the GFP siRNA/AC-cholesterol/mPEG-PLA-tocopherol containing particle is as described in the following Table 5.

TABLE 5

| particle | N/P Ratio | mPEG-PLA-tocopherol molecular weight | siRNA/AC-cholesterol amount (weight ratio) compared to mPEG-PLA-tocopherol |
|---|---|---|---|
| 1 | 6 | 2,000-1,750-530 | 0.65 |
| 2 | 4 | 2,000-1,750-530 | 0.67 |
| 3 | 3 | 2,000-1,750-530 | 0.70 |
| 4 | 6 | 5,000-4,000-530 | 0.65 |
| 5 | 4 | 5,000-4,000-530 | 0.67 |
| 6 | 3 | 5,000-4,000-530 | 0.70 |
| 7 | 18 | 2,000-1,750-530 | 1.59 |
| 8 | 12 | 2,000-1,750-530 | 1.08 |
| 9 | 9 | 2,000-1,750-530 | 0.82 |
| 10 | 18 | 5,000-4,000-530 | 1.59 |
| 11 | 12 | 5,000-4,000-530 | 1.08 |
| 12 | 9 | 5,000-4,000-530 | 0.82 |

$1 \times 10^4$ cells were divided on a 96-well cell plate, and after 24 hours, treated with 30 Nm of siRNA in the presence of 10% blood serum for 24 hours, and then, the medium was changed. After 24 hours, GFP fluorescence was measured with an ELISA reader (excitation wavelength: 485/20 nm, emission wavelength: 528/20 nm). The measurement result is shown in the following Table 6. Control was treated with phosphate buffered saline only.

TABLE 6

| particle | GFP Fluorescence (%) | Cell viability (%) | GFP fluorescence/ cell viability (%) |
|---|---|---|---|
| Control | 98.4 | 99.8 | 98.6 |
| 1 | 48.1 | 89.9 | 53.6 |
| 2 | 63.4 | 101.1 | 62.8 |
| 3 | 68.2 | 101.1 | 67.6 |
| 4 | 67.7 | 90.9 | 74.5 |
| 5 | 62.2 | 96.1 | 64.8 |
| 6 | 80.7 | 95.4 | 84.6 |
| 7 | 42.4 | 91.6 | 46.3 |
| 8 | 29.9 | 86.7 | 34.5 |
| 9 | 27.1 | 86.7 | 31.2 |
| 10 | 45.4 | 97.1 | 46.7 |
| 11 | 26.9 | 87.0 | 30.9 |
| 12 | 28.5 | 87.1 | 32.8 |

Table 6 shows results obtained by measuring GFP fluorescence, and then, calculating cell viability by SRB assay, and dividing the GFP fluorescence value by the cell viability. It can be seen from Table 6 that GFP protein expression was inhibited about 30~40%.

[Experimental Example 5] Evaluation of Activity (mRNA level) of siRNA/AC-cholesterol/mPEG-PLA-tocopherol Polymeric Micelle For the particles 1 to 3 of Experimental Example 4, the activity of siRNA/AC-cholesterol/mPEG-PLA-tocopherol polymeric micelle was confirmed at mRNA level. The polymeric micelle was treated under the same conditions as Experimental Example 4, except that the administration concentration of siRNA was varied to 15 nM and 30 nM. Cells were treated with the polymeric micelle, and after 48 hours, GFP mRNA and GAPDH mRNA were subjected to Quantitive RT-PCR to comparatively quantify GFP mRNA. Control was treated with phosphate buffered saline only. The result of quantification is shown in the following Table 7

TABLE 7

| particle | Administration concentration (nM) | GFP mRNA expression (%) |
|---|---|---|
| Control | 0 | 100.0% |
| 1 | 15 | 40.1% |
|  | 30 | 4.6% |
| 2 | 15 | 66.9% |
|  | 30 | 6.1% |
| 3 | 15 | 71.2% |
|  | 30 | 10.3% |

Table 7 shows the activities of tocopherol polymeric micelle delivery systems examined by the expression amount of mRNA. It can be seen from the Table 7 that the amount of GFP mRNA decreased in proportion to the administration amount, and that GFP mRNA was inhibited 90% or more at 30 nM.

[Experimental Example 6] Activity Comparison Experiment of siRNA Polymeric Micelle and Lipofectamine The activity of siRNA/AC-cholesterol/mPEG-PLA-tocopherol polymeric micelle and the activity of lipofectamine (Invitrogen) commercially used for cell delivery of nucleic acid were compared at protein level. The experiment was conducted by the same method as Experimental Example 4 for the particle 1 of Experimental Example 4. Control was treated with phosphate buffered saline only. The results are shown in the following Table 8.

TABLE 8

| particle | GFP fluorescence (%) | Cell viability (%) | GFP fluorescence/ cell viability (%) |
|---|---|---|---|
| control | 98.4 | 99.8 | 98.6 |
| particle 1 of Experimental Example 4 | 57.0 | 99.5 | 57.3 |
| Lipofectamine | 47.9 | 73.0 | 65.5 |

Table 7 shows the results of comparison of activities of siRNA polymeric micelle and lipofectamine examined by the amount of protein expression. It can be seen from the Table 8 that siRNA polymer inhibited expression of GFP protein with the similar level to lipofectamine while exhibiting higher cell viability. This means that siRNA polymeric micelle delivery system has more excellent activity compared to toxicity than lipofectamine.

[Experimental Example 7] In vivo activity of siRNA/AC-cholesterol/mPEG-PLA-tocopherol Polymeric Micelle It was confirmed whether siRNA/AC-cholesterol/mPEG-PLA-tocopherol polymeric micelle can inhibit target gene VEGF (vascular endothelial growth factor) of used siRNA in the living body.

A nude mouse (provided by Central Lab. Animal Inc.) was subcutaneously injected with A549 lung cancer cell line (ATCC) to prepare a cancer-induced mouse. The cancer model mouse was intravenously injected with the VEGF siRNA/AC-cholesterol/mPEG-PLA-tocopherol polymeric micelle of Example 12 at a dose of 1.5 mg/kg, and after 48 hours, cancer tissue was extracted. The extracted cancer tissue was pulverized and the amount of VEGF protein was analyzed by ELISA. The ELISA was conducted according to the instruction of kit manufacturer (R&D systems). As control, saline solution was injected. The results are shown in Table 9.

TABLE 9

| Group | Individual | VEGF concentration (pg/ml) | Relative amount (%) | average (%) |
|---|---|---|---|---|
| Control | #1 | 820.6 | 127.5 | 100.0 |
| | #2 | 475.0 | 73.8 | |
| | #3 | 610.5 | 94.9 | |
| | #4 | 668.3 | 103.8 | |

TABLE 9-continued

| Group | Individual | VEGF concentration (pg/ml) | Relative amount (%) | average (%) |
|---|---|---|---|---|
| VEGF siRNA polymeric micelle | #1 | 342.7 | 53.3 | 57.2 |
| | #2 | 344.9 | 53.6 | |
| | #3 | 356.8 | 55.4 | |
| | #4 | 427.5 | 66.4 | |

Table 9 shows inhibition rate of target gene in cancer tissue after intravenous injection of siRNA polymeric micelle delivery system in a caner model mouse. The siRNA polymeric micelle delivery system inhibited the amount of VEGF protein about 43% in the cancer tissue. It can be seen from the Table 9 that systemic delivery of siRNA may be enabled with the siRNA polymeric micelle delivery system.

[Experimental Example 8] In vivo activity of siRNA-cholesterol/AC-cholesterol/mPEG-PLA-tocopherol Polymeric Micelle The experiment was conducted by the same method as Experimental Example 7, except using VEGF siRNA-cholesterol/AC-cholesterol/mPEG-PLA-tocopherol polymeric micelle of Example 12, and then, the concentration of VEGF was analyzed. As control, a saline solution was used. The results are shown in Table 10.

TABLE 10

| Group | individual | VEGF concentration (pg/ml) | Relative amount (%) | average (%) |
|---|---|---|---|---|
| Control | #1 | 438.6 | 82.9 | 100.0 |
| | #2 | 403.7 | 76.3 | |
| | #3 | 745.6 | 140.9 | |
| siRNA-cholesterol polymeric micelle of Example 12 | #1 | 218.9 | 41.4 | 32.0 |
| | #2 | 173.1 | 32.7 | |
| | #3 | 115.3 | 21.8 | |

Table 10 shows inhibition rate of target gene in the cancer tissue after intravenous injection of siRNA-cholesterol polymeric micelle delivery system in a cancer model mouse. The siRNA-cholesterol polymeric micelle delivery system inhibited the amount of VEGF protein about 68% in the cancer tissue. It can be seen from the Table 10 that systemic delivery of siRNA may be enabled with the siRNA-cholesterol polymeric micelle delivery system.

[Experimental Example 9] Evaluation of activity (protein level) of siRNA/AC-cholesterol/mPEG-PLA-tocopherol/DOPE Polymeric Micelle The effect of addition of DOPE to siRNA/AC-cholesterol/mPEG-PLA-tocopherol polymeric micelle on the activity was examined A polymeric micelle comprising DOPE was prepared by the same method as Example 13 with the VEGF siRNA sequence of Example 12. A549 cell lines were respectively treated with the above micelle and the VEGF siRNA/AC-cholesterol/mPEG-PLA-tocopherol polymeric micelle of Example 12 by the same method as Experimental Example 4. The medium was recovered, and the concentration of released VEGF in the medium was measured by the method described in Experimental Example 7, and corrected with respect to control treated with phosphate buffered saline only. The measurement results are shown in the following Table 11.

TABLE 11

|  | control | siRNA polymeric micelle | DOPE containing siRNA polymeric micelle |
|---|---|---|---|
| VEGF concentration | 100% | 79.1% | 38.8% |
| siRNA activity (VEGF inhibition rate) | 0% | 20.9% | 61.2% |

Table 11 shows quantification of the concentration of VEGF protein released in the medium after treating the siRNA polymeric micelle. It can be seen from the Table 11 that siRNA activity largely increases from 20.9% to 61.2% by adding DOPE to the siRNA polymeric micelle.

Figure 9:
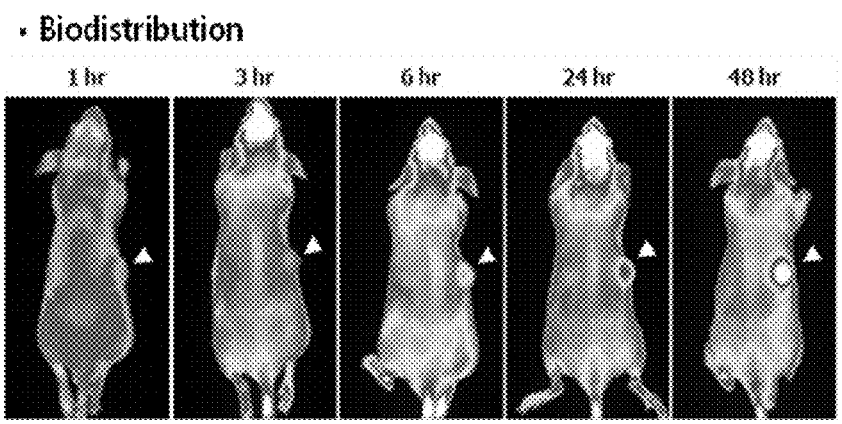
FIG. 9 is a photograph showing biodistribution of the polymeric micelle particle according to one embodiment of the present invention.

[Experimental Example 10] Evaluation of Biodistribution of siRNA/AC-cholesterol/mPEG-PLA-tocopherol/DOPE Polymeric Micelle AsPC-1 pancreatic cancer-xenografted mice were used. Cy5.5-labeled siRNA in the polymeric micelle particle was intravenously injected to the mice at a dose of 1 mg/kg. Then, its bio-distribution was investigated by measuring Cy5.5 signals with the lapse of time for 48 hours. The results are shown in FIG. 9. In FIG. 9, white triangle indicates the xenografted site. As shown in FIG. 9, the polymeric micelle particle has high tumor-specific accumulation.

What is claimed is:

1. A polymeric micelle particle, comprising:
   an anionic drug as an active ingredient;
   a lipid comprising a cationic lipid; and
   an amphiphilic block copolymer,
   wherein the anionic drug forms a complex with the cationic lipid by electrostatic interactions, and the complex of the anionic drug and the cationic lipid is entrapped in the core-shell type polymeric micelle structure of the amphiphilic block copolymer which is an A-B type di-block copolymer comprising a hydrophilic A block forming the shell and a hydrophobic B block forming the core,
   wherein the hydrophilic A block is one or more selected from the group consisting of polyalkyleneglycol, polyvinyl alcohol, polyvinyl pyrrolidone, polyacrylamide, and a derivative thereof, and the hydrophobic B block is one or more selected from the group consisting of polyester, polyanhydride, polyamino acid, polyorthoester, and polyphosphazine, and
   wherein the particle is free from a polyethyleneglycol (PEG)-lipid conjugate, and a polyamide (ATTA)-lipid conjugate,
   wherein the hydrophobic B block has a number average molecular weight of 1,000 to 50,000 Dalton,
   wherein a weight ratio of (a) the complex of the anionic drug and the cationic lipid to (b) the amphiphilic block copolymer ((a)/(b)×100) is 0.01 to 50 wt %.

2. The polymeric micelle particle of claim 1, wherein an amount of the amphiphilic block copolymer ranges from 40 to 98% by weight based on a total weight of the particle.

3. The polymeric micelle particle of claim 1, wherein an amount of the cationic lipid ranges from 0.1 to 15% by weight based on a total weight of the particle.

4. The polymeric micelle particle of claim 1, wherein a weight ratio of the amphiphilic block copolymer to the lipid ranges from 1.5 to 20.

5. The polymeric micelle particle of claim 1, wherein the anionic drug is nucleic acid.

6. The polymeric micelle particle of claim 5, wherein the nucleic acid is one or more selected from the group consisting of RNA, DNA, siRNA (short interfering RNA), aptamer, antisense ODN (oligodeoxynucleotide), antisense RNA, ribozyme, and DNAzyme.

7. The polymeric micelle particle of claim 5, wherein the nucleic acid has at least one end modified with one or more selected from the group consisting of cholesterol, tocopherol, and C10-C24 fatty acid.

8. The polymeric micelle particle of claim 1, wherein the amphiphilic block copolymer has the hydrophobic B block whose hydroxyl end group is modified with one or more selected from the group consisting of cholesterol, tocopherol, and C10-C24 fatty acid.

9. The polymeric micelle particle of claim 1, wherein the cationic lipid is one or more selected from the group consisting of N,N-dioleyl-N,N-dimethylammoniumchloride (DODAC), N,N-distearyl-N,N-dimethylammoniumbromide (DDAB), N-(1-(2,3-dioleoyloxy)propyl-N,N,N-trimethylammoniumchloride (DOTAP), N,N-dimethyl-(2,3-dioleoyloxy)propylamine (DODMA), 1,2-diacyl-3-trimethylammonium-propane (TAP), 1,2-diacyl-3-dimethylammonium-propane (DAP), 3β-[N—(N',N',N'-trimethylaminoethane)carbamoyl]cholesterol (TC-cholesterol), 3 β[N—(N',N'-dimethylaminoethane)carbamoyl]cholesterol (DC-cholesterol), 3β[N—(N'-monomethylaminoethane)carbamoyl]cholesterol (MC-cholesterol), 3β[N-(aminoethane)carbamoyl]cholesterol (AC-cholesterol), cholesteryloxypropane-1-amine (COPA), N—(N'-aminoethane)carbamoylpropanoic tocopherol (AC-tocopherol), and N—(N'-methylaminoethane)carbamoylpropanoic tocopherol (MC-tocopherol).

10. The polymeric micelle particle of claim 1, wherein the ratio of quantities of electric charges of the cationic lipid (N) and the anionic drug (P) (N/P) is 0.1 to 128.

11. The polymeric micelle particle of claim 1, wherein the hydrophilic A block is one or more selected from the group consisting of monomethoxy polyethylene glycol, monoacetoxy polyethylene glycol, polyethylene glycol, a copolymer of polyethylene and propylene glycol, and polyvinyl pyrrolidone, and the hydrophobic B block is one or more selected from the group consisting of polylactide, polyglycolide, polycaprolactone, polydioxane-2-one, a copolymer of polylactide and glycolide, a copolymer of polylactide and polydioxane-2-one, a copolymer of polylactide and polycaprolactone, and a copolymer of polyglycolide and polycaprolactone.

12. The polymeric micelle particle of claim 11, wherein the hydrophilic A block is monomethoxy polyethylene glycol, and the hydrophobic B block is polylactide.

13. The polymeric micelle particle of claim 1, wherein the hydrophilic A block has a number average molecular weight of 200 to 50,000 Dalton.

14. The polymeric micelle particle of claim 1, wherein the lipid further comprises at least one fusogenic lipid selected from the group consisting of phospholipid, cholesterol, and tocopherol.

15. The polymeric micelle particle of claim 14, wherein the phospholipid is one or more selected from the group consisting of phosphatidylethanolamine (PE), phosphatidylcholine (PC), and phosphatidic acid.

16. The polymeric micelle particle of claim 14, wherein the fusogenic lipid is one or more selected from the group consisting of dilauroyl phosphatidylethanolamine, dimyristoyl phosphatidylethanolamine, dipalmitoyl phosphatidylethanolamine, distearoyl phosphatidylethanolamine, dioleoyl phosphatidylethanolamine, dilinoleoyl phosphatidylethanolamine, 1-palmitoyl-2-oleoyl phosphatidylethanolamine, 1,2-diphytanoyl-3-sn-phosphatidylethanolamine, dilauroyl phosphatidylcholine, dimyristoyl phosphatidylcholine, dipalmitoyl phosphatidylcholine, distearoyl phosphatidylcholine, dioleoyl phosphatidylcholine, dilinoleoyl phosphatidylcholine, 1-palmitoyl-2-oleoyl phosphatidylcholine, 1,2-diphytanoyl-3-sn-phosphatidylcholine, dilauroyl phosphatidic acid, dimyristoyl phosphatidic acid, dipalmitoyl phosphatidic acid, distearoyl phosphatidic acid, dioleoyl phosphatidic acid, dilinoleoyl phosphatidic acid, 1-palmitoyl-2-oleoyl phosphatidic acid, 1,2-diphytanoyl-3-sn-phosphatidic acid, cholesterol, and tocopherol.

* * * * *